United States Patent [19]

Durette

[11] 4,324,900
[45] Apr. 13, 1982

[54] 3-AMINO-4-C-CARBOXY-2,3,4,6-TETRADEOXY-D-ARABINO-HEXOSE TRIMETHYLENE DITHIOACETAL

[75] Inventor: Philippe L. Durette, New Providence, N.J.

[73] Assignee: Merck & Co., Inc., Rahway, N.J.

[21] Appl. No.: 248,176

[22] Filed: Mar. 30, 1981

[51] Int. Cl.³ ............... C07C 149/243; C07D 339/00; C07D 339/06; C07D 339/08
[52] U.S. Cl. ...................................... 549/11; 549/22; 549/39; 549/89; 562/426; 562/556
[58] Field of Search ..................... 549/11, 22, 39, 89; 562/426, 556

[56] References Cited

U.S. PATENT DOCUMENTS 4,234,596 11/1980 Christensen et al. ............ 424/274

FOREIGN PATENT DOCUMENTS 79101307 5/1979 European Pat. Off. .

OTHER PUBLICATIONS

Hanessian et al., Absts. Papers, 181st ACS National Meeting, CARB 27 (1981).

Primary Examiner—Richard Raymond
Attorney, Agent, or Firm—Frank M. Mahon; James A. Arno; Hesna J. Pfeiffer

[57] ABSTRACT

Disclosed is a chiral, total synthesis of thienamycin from D-glucose, which proceeds via intermediates I, II, and III and joins aldehyde IV or acid V, which are known to be useful in the total synthesis of thienamycin (VI):

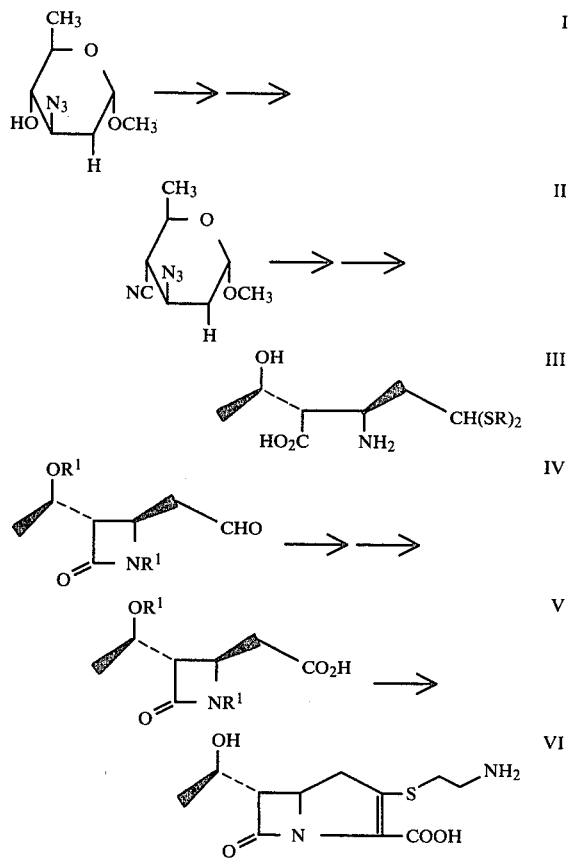

wherein
$R^1$ is hydrogen or a removable protecting group;
R is lower alkyl having 1-6 carbon atoms or bi-valent alkyl having 2-6 carbon atoms which joins the two sulfur atoms.

1 Claim, No Drawings

3-AMINO-4-C-CARBOXY-2,3,4,6-TETRADEOXY-D-ARABINO-HEXOSE TRIMETHYLENE DITHIOACETAL

BACKGROUND OF THE INVENTION

This invention relates to the chiral, total synthesis of thienamycin from D-glucose (dextrose).

In its broadest terms, the process proceeds from D-glucose via intermediates I, II, and III and

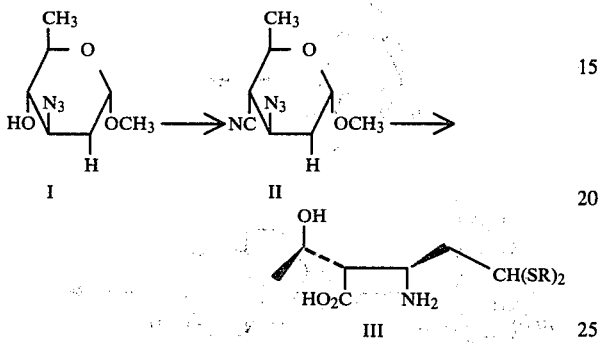

encounters aldehyde IV or acid V, which are known to be useful in the total synthesis of thienamycin (VI).

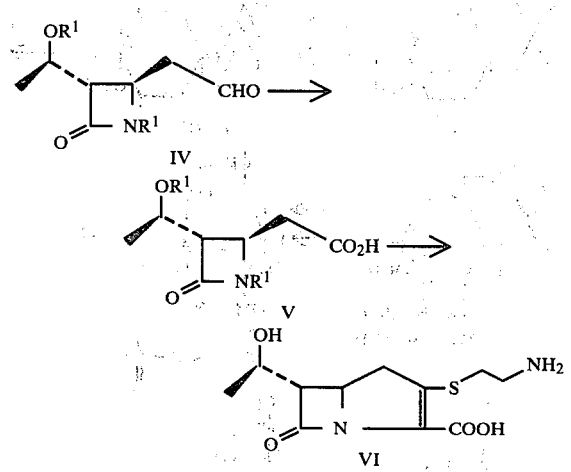

wherein: R is alkyl having 1–6 carbon atoms or the two sulfur atoms may be joined to form a ring comprising R; $R^1$ is hydrogen or a removable protecting group, such as a triorganosilyl group, $(R°)_3Si-$ wherein R° values are independently chosen from alkyl having 1–6 carbon atoms, aryl and aralkyl having 6–10 carbon atoms.

The transformations IV→V, IV→VI, and V→VI are known. See for example: U.S. patent application Ser. No. 112,058 (filed Jan. 14, 1980, now abandonded); U.S. Pat. No. 4,234,596 (issued Nov. 18, 1980); and EPO application No. 79202307.1 (filed May 1, 1979; Publication Number No. 007973), which publications and pending application disclose schemes of total synthesis which can be fed by common imtermediates made available by the presently disclosed and claimed process. For the same purpose, the following co-pending, concurrently filed, commonly assigned U.S. patent applications Ser. Nos. 248,174; 248,175; 248,177; and 248,178 are also incorporated by reference.

DETAILED DESCRIPTION OF THE INVENTION

The process of the present invention may conveniently be represented by the following reaction diagram:

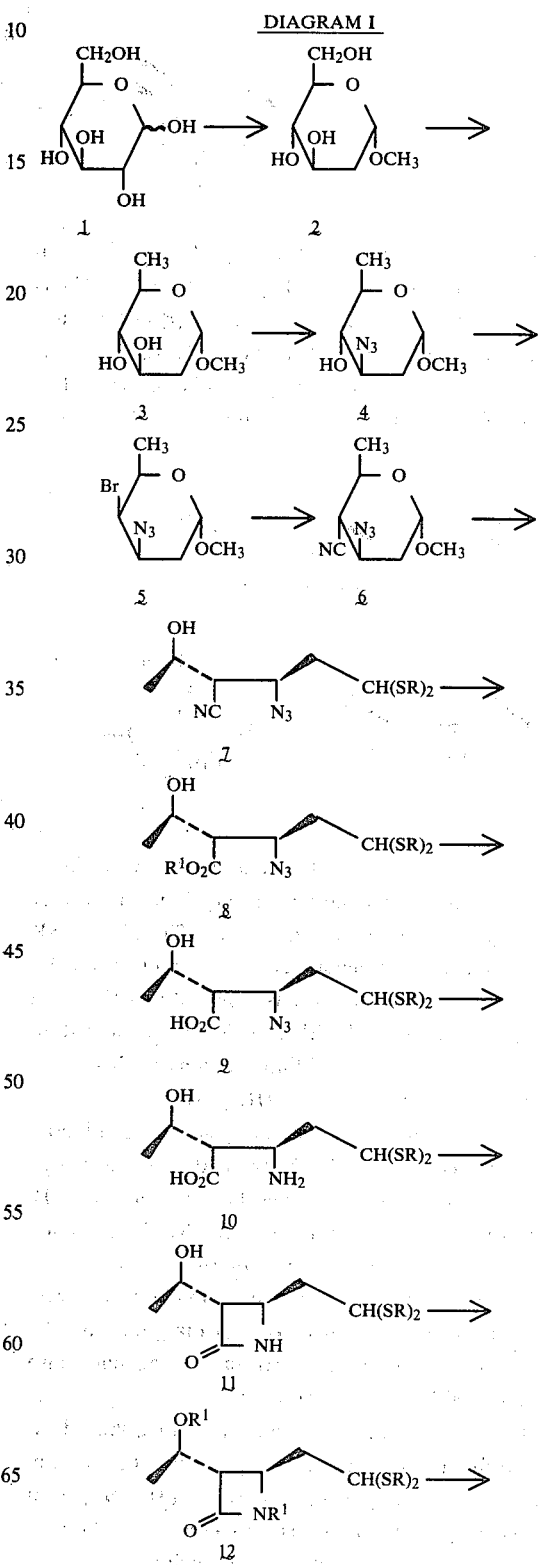

-continued
DIAGRAM I

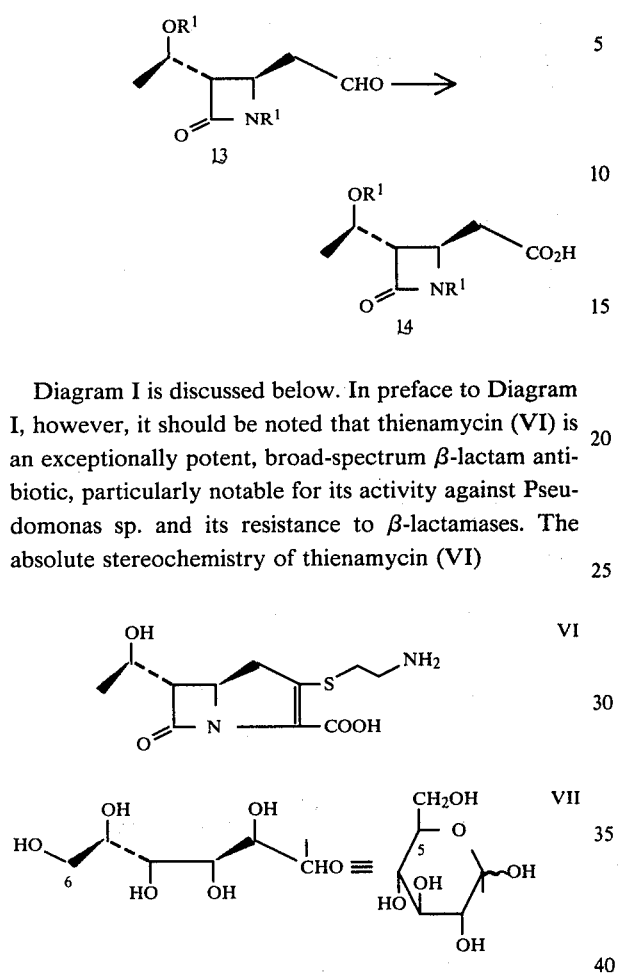

Diagram I is discussed below. In preface to Diagram I, however, it should be noted that thienamycin (VI) is an exceptionally potent, broad-spectrum β-lactam antibiotic, particularly notable for its activity against Pseudomonas sp. and its resistance to β-lactamases. The absolute stereochemistry of thienamycin (VI)

is 5R, 6S, 8R. The present invention affords a chiral, total synthesis of thienamycin starting from the readily available sugar, D-glucose (dextrose). The 5R, 6S, 8R stereochemistry of thienamycin is inherent in the D-glucose structural symmetry, as depicted in VII (chiral centers 3, 4, and 5). D-Glucose is functionalized to afford optically active azetidinone aldehyde IV or acid V, via intermediates I, II, and III, above.

A key intermediate in the conversion of D-glucose into azetidinone aldehyde IV or acid V is methyl 3-azido-2,3,6-trideoxy-α-D-arabino-hexopyranoside (I). Intermediate I is transformed into methyl 3-azido-4-C-cyano-2,3,4,6-tetradeoxy-α-D-arabino-hexopyranoside (II), which is then converted, as depicted in the diagram below and in words relative to that diagram, into the open amino acid dithioacetal III and subsequently into azetidinone aldehyde IV and acid V.

Methyl 3-azido-2,3,6-trideoxy-α-D-arabino-hexopyranoside (4) is obtained either from methyl 2,6-dideoxy-α-D-arabino-hexopyranoside (3) or from methyl α-D-glucopyranoside (12), as represented by the following reaction diagrams, respectively:

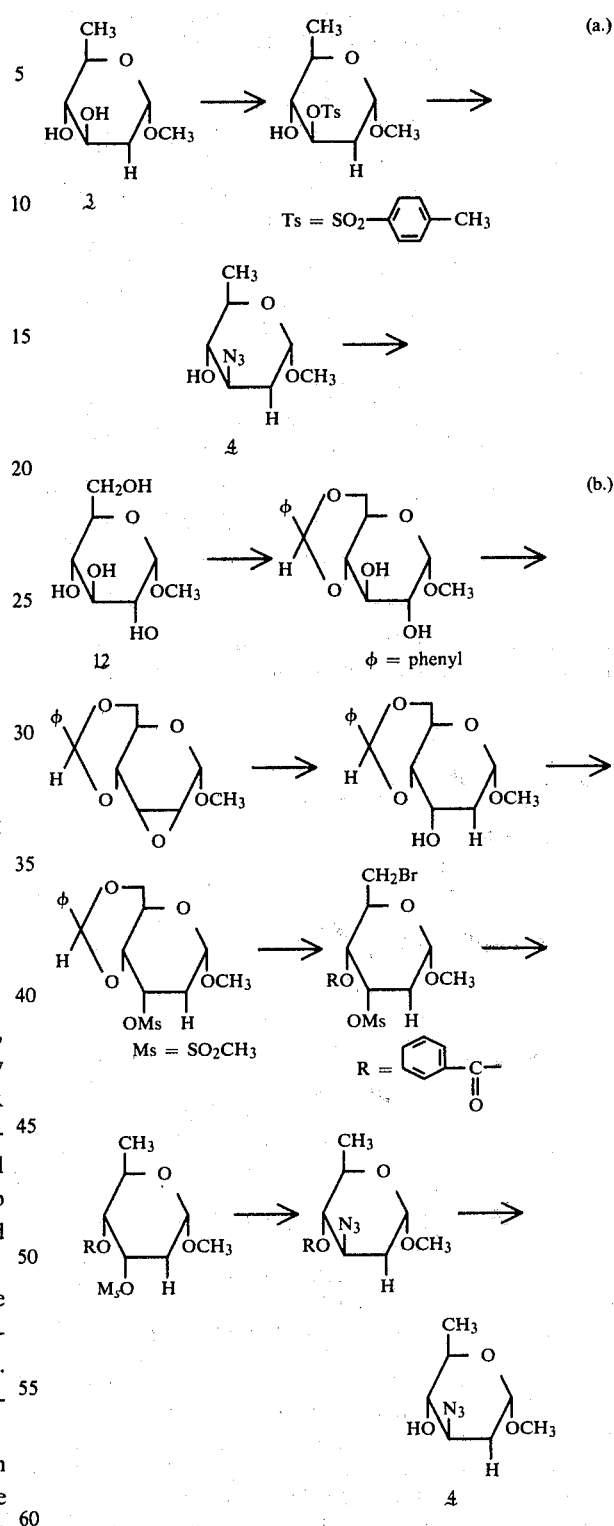

Methyl 2,6-dideoxy α-D-arabino-hexopyranoside (3) is obtained from D-glucose (1), via 2-deoxy-D-glucose (13) or D-glucal (14) and methyl 2-deoxy-α-D-glucopyranoside (2), as represented by the following reaction diagram:

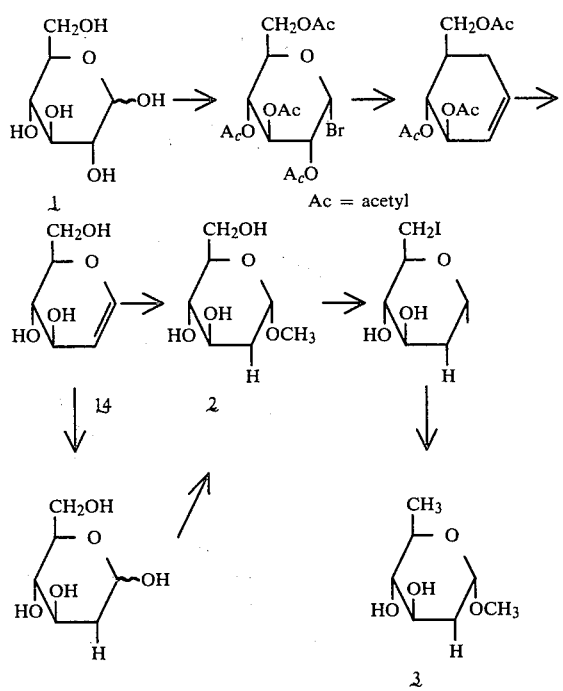

Methyl α-D-glucopyranoside (12) is obtained from D-glucose (1) as shown below,

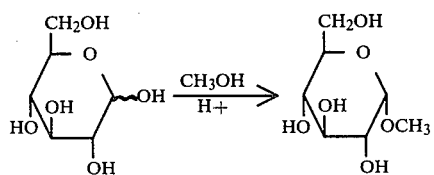

Now, returning to Diagram I, above, the transformation 1→2 is known. Typically D-glucose (1) is converted into methyl 2-deoxy-α-D-glucopyranoside (2) by the following sequence of reactions: (a) acetic anhydride and pyridine or acetic anhydride and sodium acetate to give penta-O-acetyl-D-glucopyranose; (b) hydrogen bromide in acetic acid to afford tetra-O-acetyl-α-D-glucopyranosyl bromide; (c) zinc and acetic acid to yield tri-O-acetyl-D-glucal; (d) sodium (or sodium methoxide) in methanol to give D-glucal; and (e) methanolic hydrogen chloride to yield 2. Conversion of D-glucal (or 2-deoxy-D-glucose) into 2 is reported in I. W. Hughes, et. al., *J. Chem. Soc.*, 2846 (1949).

The transformation 2→3 is accomplished by treating 2 in a solvent such as toluene, benzene, dimethylformamide, dichloromethane, or the like with an iodinating agent (or other halogenating agent), such as methyltriphenoxyphosphonium iodide, iodotriphenoxyphosphonium iodide, triphenyphosphine-N-iodosuccinimide; triphenylphosphinetetraiodomethane; triphenylphosphine-2,4,5-triiodoimidazole; triphenylphosphine, iodine, and imidazole; or the like at a temperature of from 20° to 100° C. for from 1 to 24 hours.

The hydrogenolysis to yield compound 3 is typically conducted in a solvent, such as methanol, ethanol, ethyl acetate, or the like, at a temperature of from 20° to 50° C. in the presence of a catalyst such as Raney nickel, palladium-on-charcoal, palladium black, palladium hydroxide, or the like, under a hydrogen pressure of from 1 to 5 atmospheres.

Transformation 3→4 is accomplished in a solvent such as pyridine or dichloromethane, chloroform, or the like with p-toluenesulfonyl chloride, p-toluenesulfonic anhydride, or the like in the presence of a base such as Et$_3$N, iPr$_2$NEt, pyridine, 4-dimethylaminopyridine, or the like, at a temperature of from −15° C. to +10° C. for from 24 hours to 10 days to yield the C-3 tosylate, which upon treatment, in a solvent such as ethanol, methanol, or the like, with alcoholic base, such as ethanolic sodium hydroxide, ethanolic potassium hydroxide, methanolic sodium hydroxide, methanolic potassium hydroxide, or the like, followed by treatment with an alkali azide, such as lithium azide, sodium azide, potassium azide, or the like in the presence of ammonium chloride at a temperature of from 50° C. to 100° C. from 1 hour to 24 hours yields the azide 4.

Treatment of 4 in a solvent such as dichloromethane, chloroform, or the like with trifluoromethanesulfonyl chloride, trifluoromethanesulfonic anhydride, or the like in the presence of a base such as Et$_3$N, iPr$_2$NEt, pyridine, 4-dimethylaminopyridine or the like at a temperature of from −76° C. to 0° C. for from 20 minutes to 2 hours, followed by treatment with a brominating agent, such as lithium bromide, sodium bromide, tetraethylammonium bromide, tetra-n-butylammonium bromide or the like in a solvent such as, dichloromethane, acetonitrile tetrahydrofuran, dimethylformamide, or the like at a temperature of from 20° C. to 100° C. for from 30 minutes to 5 hours, yields the 4-bromo-4-deoxy sugar 5 which upon treatment with sodium cyanide, potassium cyanide (in the presence or absence of a crown ether), tetraethylammonium cyanide, tetra-n-butylammonium cyanide, tetraethylammonium chloride-sodium cyanide, or the like in a solvent such as dichloromethane, acetonitrile, tetrahydrofuran, dimethylformamide, dimethylsulfoxide, hexamethylphosphoramide, or the like at a temperature of from 30° C. to 150° C. for from 15 minutes to 24 hours yields compound 6.

Transformation 6→7 is accomplished by treating 6 in a mineral acid such as hydrochloric acid, sulfuric acid, or the like with an alkanethiol, such as methanethiol, ethanethiol, propanethiol, or the like, or an alkanedithiol, such as 1,2-ethanedithiol; 1,3-propanedithiol, or the like at a temperature of from 0° to 30° C. for from 30 minutes to 24 hours. The value of R is determined by the identity of the thiol taken in reaction.

Alcoholysis 7→8 is accomplished by treating 7 either (a) in an alcohol such as methanol, ethanol, isopropanol, or the like with an alkali alkoxide, such as sodium methoxide, sodium ethoxide, sodium isopropoxide, or the like, at a temperature of from 0° to 30° C. for from 1 to 24 hours, followed by neutralization with a cation-exchange resin in the H$^+$ cycle, such as Amberlite IR-120 (H$^+$), Bio-Rad AG 50W, Dowex 50W, or the like; or (b) in a solvent such as diethyl ether, dichloromethane, chloroform, or the like with an alcohol, such as methanol, ethanol, isopropanol, or the like, saturated at 0° C. with dry hydrogen chloride gas, at a temperature of from 0° to 30° C. for from 2 to 24 hours, followed by hydrolysis at 0° C. The value of R$^1$ is determined by the identity of the alcohol taken in reaction.

Hydrolysis 8→9 is effected in aqueous alcohol, such as methanol, ethanol, or the like with an equivalent amount of a base such as NaOH, KOH, Ba(OH)$_2$, Na$_2$-

$CO_3$, or the like at a temperature of from 25° to 100° C. for from 1.0 minute to 10 hours.

Conversion of azido acid 9 into amino acid 10 is accomplished by treating 9 in a solvent, such as methanol, ethanol, ethyl acetate, acetic acid, or the like, at a temperature of from 20° to 50° C. in the presence of a catalyst such as palladium-on-charcoal, palladium black, palladium-on-barium sulfate, platinum oxide, or the like under a hydrogen pressure of from 1 to 5 atmospheres.

The transformation 10→11 is accomplished by treating 10 with dicyclohexylcarbodiimide (DCC), or the like, in the presence of a base such as triethylamine, 4-dimethylaminopyridine, pyridine, or the like.

The transformation 11→12 establishes the protecting group $R^1$. The most preferred protecting groups $R^1$ are triorganosilyl groups such as t-butyldimethylsilyl, t-butyldiphenylsilyl, triphenylsilyl, isopropyldimethylsilyl, and the like. Typically, silylation is accomplished by treating 11 with the corresponding triorganosilyl chloride in a solvent such as dimethylformamide, hexamethylphosphoramide, acetonitrile, tetrahydrofuran, and the like at a temperature of from −20° to 80° C. for from 0.5 to 24 hours in the presence of a base such as triethylamine, diisopropylethylamine, or imidazole.

The transformation 12→13 is accomplished by treating 12 in a solvent such as aqueous THF, aqueous acetone, aqueous acetonitrile, aqueous p-dioxane, or the like with a Lewis acid, such as mercuric oxide, mercuric chloride, boron trifluoride-etherate, thallium trinitrate, silver tetrafluoroborate, or the like at a temperature of from 0° to 50° C. for from 1 to 24 hours.

Conversion of aldehyde 13 into acid 14 is accomplished with an oxidizing agent, such as Jones reagent ($CrO_3$, $H_2SO_4$ in acetone), potassium permanganate in pyridine, silver oxide, bromine, or the like.

In the foregoing word description of the above schematic reaction diagram for the total synthesis of thienamycin, it is to be understood that there is considerable latitutde in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation.

EXAMPLE 1

STEP A

Preparation of 3-Azido-4-C-cyano-2,3,4,6-tetradeoxy-D-arabino-hexose trimethylene dithioacetal

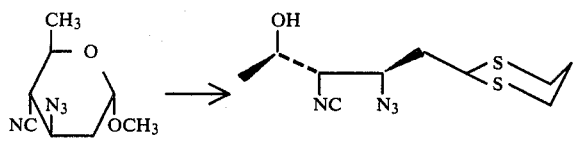

Methyl 3-azido-4-C-cyano-2,3,4,6-tetradeoxy-α-D-arabino-hexopyranoside (979 mg, 4.99 mmol) is treated with concentrated hydrochloric acid (210 ml) for 5 minutes at room temperature, at which time 1,3-propanedithiol (1.0 ml, 9.96 mmol) and sufficient methanol to achieve solution are added. After the reaction mixture is stirred for 1 hour at room temperature, the methanol is removed by evaporation under vacuum, and the product is extracted with dichloromethane. The combined organic extracts are evaporated under vacuum, and the residue is chromatographed on a column of silica gel (Merck No. 7734) (1:1 diethyl ether-hexane) to yield 1.29 g (95%) of the trimethylene dithioacetal as a white crystalline solid, $^1$H NMR (300 MHz, $CDCl_3$): 1.50 (d,C—$CH_3$) 1.76 (d, OH-5, $J_{OH,H\text{-}5}$ 5 Hz), 1.92 (m, 1H, dithiane H-4), 2.07 (septet, H-2), 2.17 (m, 1H, dithiane H-4'), 2.27 (septet, H-2'), 2.68 (dd, H-4, $J_{3,4;\ 4,5}$ 3.2, 9 Hz), 2.84–3.00 (m, 4H, dithiane H-3's), 4.14–4.26 (m, 2H, H-1, H-5), 4.34 ppm (m, H-3); mass spectrum m/e 272 (M).

STEP B

3-Azido-4-C-carbomethoxy-2,3,4,6-tetradeoxy-D-arabino-hexose trimethylene dithioacetal

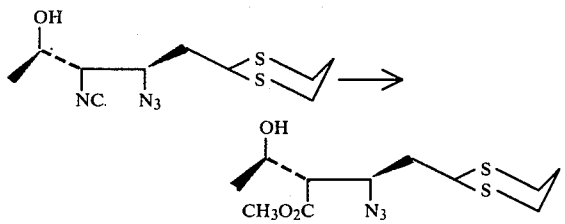

Dry hydrogen chloride gas is bubbled for 1 hour through a solution of 3-azido-4-C-cyano-2,3,4,6-tetradeoxy-D-arabino-hexose trimethylene dithioacetal (1.28 g, 4.71 mmol) in diethyl ether (7.3 ml) and absolute methanol (7.3 ml) cooled in an ice-bath. The solution is then allowed to stand overnight at room temperature and evaporated under vacuum. The residue is taken up in dichloromethane, washed with saturated sodium hydrogen carbonate solution, and evaporated. The resulting material is chromatographed on a column of silica gel (Merck No. 7734) (10:1 diethyl ether-hexane) to afford 1.08 g (75%) of the desired azido ester trimethylene dithioacetal; IR ($CHCl_3$):1733 (C═O), 2095 ($N_3$); $^1$H NMR (300 MHz, $CDCl_3$): 3.79 (s, 3H, $CO_2CH_3$).

STEP C

3-Azido-4-C-carboxy-2,3,4,6-tetradeoxy-D-arabino-hexose trimethylene dithioacetal

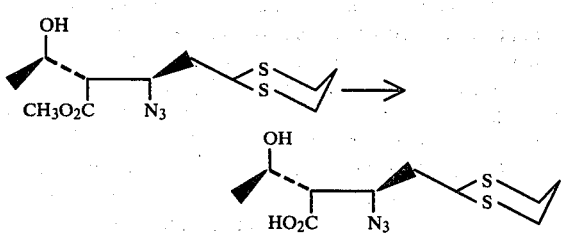

To a solution of 3-azido-4-C-carbomethoxy-2,3,4,6-tetradeoxy-D-arabino-hexose trimethylene dithioacetal (1.07 g, 3.50 mmol) in methanol (2 ml) is added a solution of sodium hydrogen carbonate (403 mg) in water (1.4 ml). To the mixture is added dropwise with stirring at room temperature 0.1 N aqueous sodium hydroxide until a constant pH of 11 is reached. Subsequently the mixture is brought to pH 7.3 with 50% sulfuric acid, and extracted with diethyl ether. The aqueous layer is brought to pH 3 at 0° and extracted rapidly (3×) with diethyl ether. The combined organic extracts are dried (magnesium sulfate) and evaporated under vacuum to yield 939 mg (92%) of the azido acid trimethylene dithioacetal; IR (CHCl$_3$): 2095 (N$_3$).

STEP D

3-Amino-4-C-carboxy-2,3,4,6-tetradeoxy-D-arabino-hexose trimethylene dithioacetal

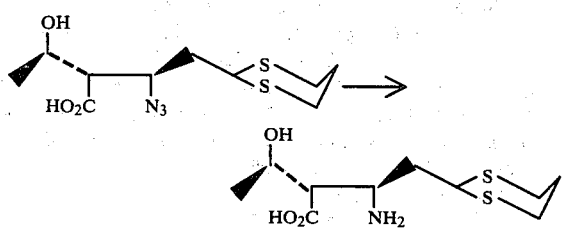

A mixture of 3-azido-4-C-carboxy-2,3,4,6-tetradeoxy-D-arabino-hexose trimethylene dithioacetal (920 mg, 3.01 mmol) and 5% palladium-on-charcoal (375 mg) in methanol (25 ml) is hydrogenated at a pressure of 1 atmosphere for 5 hours at room temperature. The catalyst is then removed by filtration through Celite and the filtrate evaporated and dried in vacuo to give TLC-chromatographically-homogeneous, ninhydrin-positive amino acid trimethylene dithioacetal; yield 816 mg (97%).

STEP E

3α-[(1'R)-hydroxyethyl]-4β-[2',2'-(1,3-propanedithio)-ethyl]-2-azetidinone

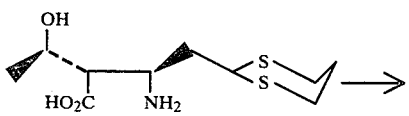

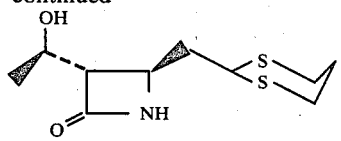

A mixture of 3-amino-4-C-carboxy-2,3,4,6-tetradeoxy-D-arabino-hexose trimethylene dithioacetal (810 mg, 3.05 mmol) in acetonitrile (15 ml) is treated with N,N'-dicyclohexylcarbodiimide (689 mg, 3.34 mmol). The resulting mixture is kept at room temperature for 10 minutes and then heated at 60° for 5 hours. The reaction mixture is concentrated, the residue is slurried in ethyl acetate, and the precipitated urea is removed by filtration. The filtrate is washed successively with N aqueous hydrochloric acid, saturated aqueous sodium hydrogen-carbonate, water, dried (magnesium sulfate), and evaporated under vacuum to yield 385 mg (51%) of the desired 2-azetidinone trimethylene dithioacetal.

STEP F

3α-[(1'R)hydroxyethyl]-4β-(2'-oxoethyl)-2-azetidinone

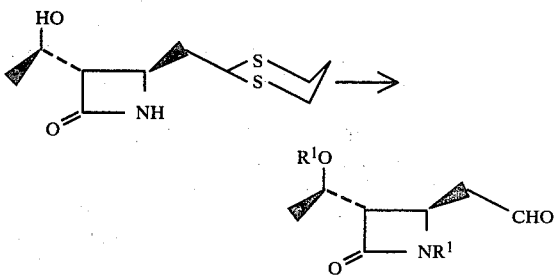

To a suspension of red mercuric oxide (3.5 equiv.) and boron trifluoride-etherate (3 equiv.) in 17% aqueous acetone (10 ml) is added with stirring under nitrogen a solution of 3α-[(1'R)-hydroxyethyl]-4β-[2',2'-(1,3-propanedithio)-ethyl]-2-azetidinone (381 mg, 1.54 mmol) in tetrahydrofuran (3 ml). After stirring for 24 hours, water (4 ml) and acetone (8 ml) are added and the mixture neutralized with sodium bicarbonate. The precipitate is filtered, the filtrate concentrated and extracted several times with chloroform. The organic extracts are washed with brine, dried (magnesium sulfate), and evaporated in vacuo to afford the desired aldehyde azetidinone (R$^1$=H).

Oxidation of 3α-[(1'R)-t-butyldimethylsilyloxyethyl]-4β-(2'-oxoethyl)-1-(t-butyldimethylsilyl)-2-azetidinone with Jones reagent affords optically active 3α-[(1'R)-t-butyldimethylsilyloxyethyl]-4β-(2'-carboxymethyl)-1-(t-butyldimethylsilyl)-2-azetidinone.

EXAMPLE 2

Process for preparing Methyl 3-azido-4-C-cyano-2,3,4,6-tetradeoxy-α-D-arabinohexopyranoside

STEP A

Methyl 2,6-dideoxy-3-O-(p-toluenesulfonyl)-α-D-arabinohexopyranoside

To a solution of methyl 2,6-dideoxy-α-D-arabinohexopyranoside (6.3 g, 38.8 mmol) in pyridine (200 ml)

at 0° C. is added freshly recrystallized p-toluenesulfonyl chloride (7.6 g, 39.9 mmol). The mixture is kept 5 days at 0° C., at which time additional p-toluenesulfonyl chloride (1.9 g) is added. After 3 days at 5° C., the mixture is poured into ice-water, extracted several times with dichloromethane, the combined organic extracts evaporated under vacuum, coevaporated several times with toluene, and chromatographed on silica gel (Merck No. 7734) (1:2 diethyl ether-petroleum ether, b.p. 35°-60° C.) to yield 8.5 g (69%) of the product as a solid; 'H NMR (300 MHz, CDCl$_3$): 1.30 (d, C—CH$_3$), 1.83 (td, H-2ax, J-H-1, H-2ax, 3.5 Hz, J H2eq, H2ax 12.8 Hz), 2.09 (m, H-2eq, J H-1, H-2eq 1.1 Hz, J H-2eq, H-3 5.5 Hz), 2.46 (s, ArCH$_3$), 2.53 (d, OH), 3.27 (s, OCH$_3$), 3.32 (td, H-4, $J_{H-4,H-5}=J_{H-4,H-3}=8.8$ Hz), 3.65 (m, H-5), 4.68 (broad d, H-1), 4.74 (ddd, H-3), 7.38 (d, 2H, Ar), 7.85 ppm (d, 2H, Ar); mass spectrum m/e 285 (M—OCH$_3$), 272 (M—CH$_3$CHO).

Anal. C, H, S.

STEP B

Methyl 3-Azido-2,3,6-tredeoxy-α-D-arabino-hexopyranoside

To a solution of methyl 2,6-dideoxy-3-O-(p-toluenesulfonyl)-α-D-arabino-hexopyranoside (8.4 g, 26.6 mmol) in absolute ethanol (80 ml) is added phenolphthalein (as an indicator) and subsequently dropwise at 60° C. saturated ethanolic sodium hydroxide until color persists for 10 minutes. The reaction mixture is then cooled to 10° C., the precipitated sodium tosylate removed by filtration, the filtrate brought to pH 7 with 2 N hydrochloric acid. Sodium azide (4.9 g) and ammonium chloride (2.9 g) are then added, and the mixture is stirred overnight at reflux temperature. After concentration, the residue is partitioned between dichloromethane and water, the aqueous layer extracted with dichloromethane, the combined organic extracts evaporated under vacuum, and chromatographed on silica gel (Merck No. 7734) (30:1 chloroformethyl acetate) to afford the pure product as a colorless syrup; yield 3.7 g (74%); 'H NMR (300 MHz, CDCl$_3$): 1.30 (d, C—CH$_3$), 1.73 (td, H-2ax, $J_{H-1,H-2ax}$ 3.6 Hz), 2.17 (m, H-2eq, $J_{H-1, H-2eq}$ 1.2 Hz, $J_{H-2eq, H-3}$ 5 HZ), 3.14 (t, H-4, J-$_{H-3, H-4}=J_{H-4, H-5}=9$ Hz), 3.34 (s, OCH$_3$), 3.63-3.79 (m, H-3,5), 4.75 (broad d, H-1); mass spectrum m/e 187 (M), 156 (M—OCH$_3$), 145 (M—N$_3$), 143 (M—CH$_3$CHO).

STEP C

Methyl 3-azido-4-bromo-2,3,4,6-tetradeoxy-α-D-lyxohexopyranoside

To a solution of methyl 3-azido-2,3,6-trideoxy-α-D-arabino-hexopyranoside (3.6 g, 19.2 mmol) in dichloromethane (100 ml) cooled in an ice-bath are added pyridine (2 ml) and dropwise a solution of trifluoromethanesulfonic anhydride (3.2 ml, 19.0 mmol) in dichloromethane (25 ml). After stirring for 10 minutes at 0° C. with exclusion of moisture, additional pyridine (2 ml) and trifluoromethanesulfonic anhydride (2.6 ml) are added. After 10 minutes at 0° C., the reaction mixture is diluted with dichloromethane (130 ml) and poured into a separatory funnel containing ice-water. The organic layer is separated and washed with cold N hydrochloric acid, saturated sodium hydrogen-carbonate, water, and dried (sodium sulfate). Evaporation under vacuum gives the 4-trifluoromethanesulfonate that is dissolved in dry acetonitrile (50 ml) and treated with tetra-n-butylammonium bromide (12.7 g, 39.4 mmol) for 1 hour at 40° C. The reaction mixture is concentrated, the residue partitioned between dichloromethane and water, the organic layer evaporated under vacuum and the resulting syrup chromatographed on a column of silica gel (Merck No. 7734) (1:2 dichloromethane-hexane) to yield 3.65 g (76%) of the bromide; 'H NMR (300 MHz, CDCl$_3$): 1.32 (d, C—CH$_3$), 1.90 (dd, H-2eq), 2.20 (td, H-2ax), 3.36 (s, OCH$_3$), 3.84–4.00 (m, H-3,5), 4.27 (d, H-4), 4.86 ppm (d, H-1); mass spectrum m/e 250 (M).

STEP D

Methyl 3-azido-4-C-cyano-2,3,4,6-tetradeoxy-α-D-arabino-hexopyranoside

To a solution of methyl 3-azido-4-bromo-2,3,4,6-tetradeoxy-α-D-lyxo-hexopyranoside (3.5 g, 14.0 mmol) in freshly distilled acetonitrile (75 ml) is added tetra-n-butylammonium cyanide (7.5 g, 28.0 mmol). The reaction mixture is stirred for 1 hour at 50° C., cooled, partially concentrated (25 ml), diluted with dichloromethane (250 ml), washed with water (3×), dried (sodium sulfate), and evaporate under vacuum. The residue is chromatographed on a column of silica gel (Merck No. 7734) (1:10 diethyl ether-hexane) to yield 687 mg (25%) of the desired cyanide as a colorless syrup; 'H NMR (300 MHz, CDCl$_3$): 1.42 (d, C—CH$_3$), 1.60 td, H-2ax, $J_{H-1,H-2ax}$ 3.5 Hz), 2.21 (m, H-2eq, $J_{H-1, H-2eq}$ 1.2 Hz, $J_{H-2eq, H-3}$ 5 Hz), 2.26 (t, H-4, $J_{H-3, H-4}=J_{H-4, H-5}=10.8$ Hz), 3.36 (s, OCH$_3$), 3.92–4.06 (m, H-3,5), 4.85 (broad d, H-1); mass spectrum m/e 165 (M—OCH$_3$), 154 (M—N$_3$), 152 (M—CH$_3$CHO).

What is claimed is:

1. A compound selected from:

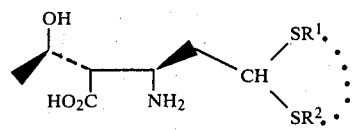

wherein: R$^1$ and R$^2$ are independently selected from alkyl having 1–6 carbon atoms, phenylalkyl having 7–10 carbon atoms; or R$^1$ and R$^2$ may be jointed as indicated by the dotted line.

* * * * *